United States Patent [19]
Yoshimoto et al.

[11] Patent Number: 5,993,855
[45] Date of Patent: Nov. 30, 1999

[54] DELAYED DRUG-RELEASING MICROSPHERES

[75] Inventors: Takashi Yoshimoto, Senndai; Masahiro Tajima; Kazuo Watabe, both of Yokohama, all of Japan

[73] Assignee: Shiseido Company, Ltd., Japan

[21] Appl. No.: 08/710,648

[22] Filed: Sep. 18, 1996

[30] Foreign Application Priority Data

Sep. 18, 1995 [JP] Japan .................................. 7-262048

[51] Int. Cl.⁶ ..................................................... A61K 9/14
[52] U.S. Cl. ......................... 424/489; 424/490; 424/468; 424/457
[58] Field of Search ................................... 424/489, 488, 424/468, 457

[56] References Cited

FOREIGN PATENT DOCUMENTS

| | | |
|---|---|---|
| 0330180 | 2/1988 | European Pat. Off. . |
| 0 292 710 | 11/1988 | European Pat. Off. . |
| 0 330 180 | 8/1989 | European Pat. Off. . |
| 0 582 459 | 2/1994 | European Pat. Off. . |
| 0 645 136 | 3/1995 | European Pat. Off. . |
| WO91/12882 | 9/1991 | WIPO . |

OTHER PUBLICATIONS

H.T. Wang et al., *Journal of Controlled Release*, 17(1), 23–32 (1991).
H.K. Sah et al., *Journal of Microencapsulation*, 12(1), 59–69 (1995).

*Primary Examiner*—Thurman K. Page
*Assistant Examiner*—William E. Benston, Jr.
*Attorney, Agent, or Firm*—Wenderoth, Lind & Ponack, L.L.P.

[57] ABSTRACT

Microspheres prepared by emulsifying an aqueous phase containing a drug and an oil phase containing a biodegradable polymer to form a W/O emulsion, and then mixing and agitating this emulsion with another aqueous phase constituting a continuous phase to form a W/O/W emulsion. These microspheres can release a major portion of the drug after a predetermined period of time has elapsed after their administration to the patient, and are especially suitable for intracerebral implantation.

11 Claims, 5 Drawing Sheets

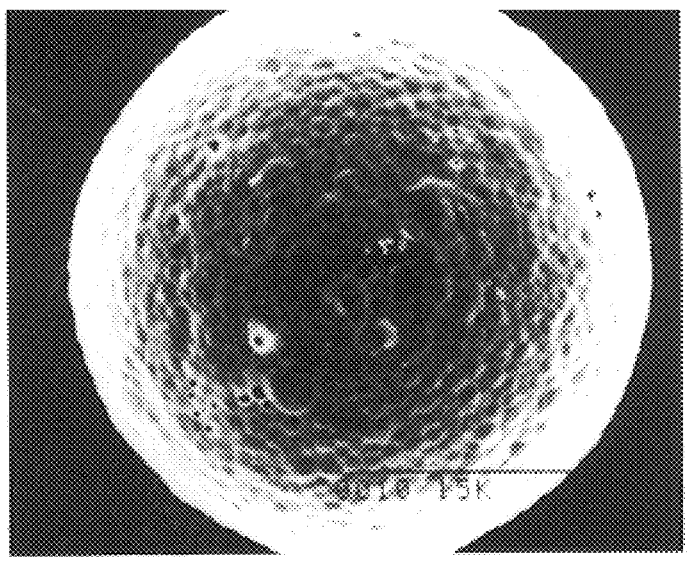
FIG. 1A  MS-16 (L)
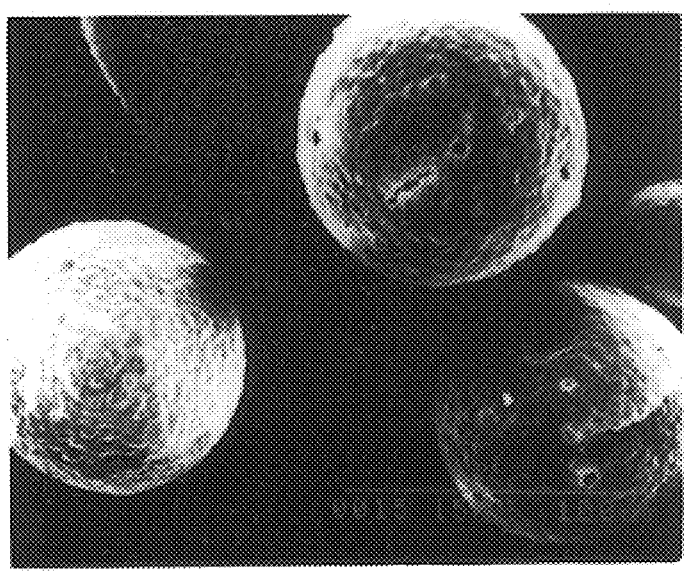
FIG. 1B  MS-16 (M)
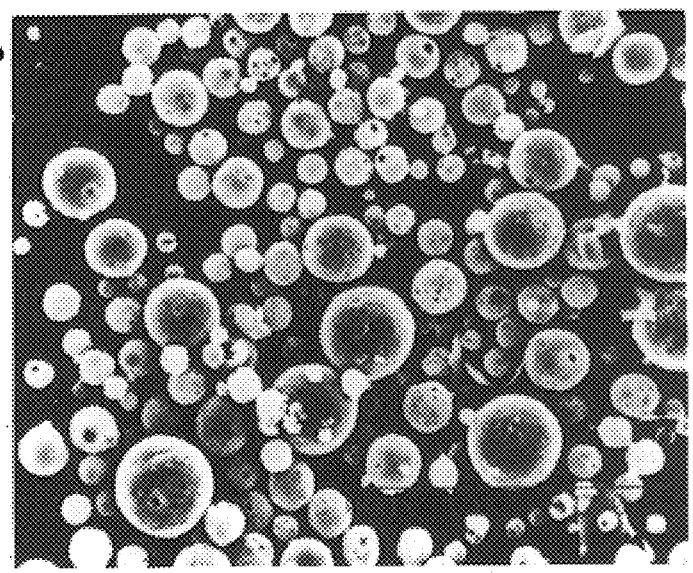
FIG. 1C  MS-16 (S)

DELAYED DRUG-RELEASING MICROSPHERES

BACKGROUND OF THE INVENTION

1. Field of the Invention

This invention relates to microspheres capable of releasing a drug after a predetermined period of time. More particularly, it relates to microspheres which are adapted for intracerebral implantation having the purpose of suppressing cerebral vasospasm.

2. Description of the Prior Art

As microcapsules or microspheres used for the purpose of releasing a drug gradually over a long period of time, a great variety of pharmaceutical preparations made by supporting drugs on various carriers and polymeric matrices have been proposed.

Typical processes for the production of such pharmaceutical preparations include, for example, a process involving the formation of a W/O/W emulsion as described in Japanese Patent Laid-Open No. 201816/'87. Moreover, processes developed with a view to overcoming the disadvantages of such production process (e.g., a low degree of drug incorporation into the polymeric matrix, and a premature burst of the drug from microspheres) have also be proposed (see Japanese Patent Laid-Open Nos. 145046/'94 and 32732/'94).

However, these pharmaceutical preparations have the common purpose of releasing the drug steadily from the carrier over a long period of time, and successful examples of such release have been disclosed.

On the other hand, prolonged drug-releasing type pharmaceutical preparations which are to be implanted in particular organs for the purpose of treating special diseases have also be proposed. As a specific example of such pharmaceutical preparations, Japanese Patent Application No. 50953/'94 discloses a pharmaceutical preparation which uses a complex of a water-soluble polymer, an oil, a fatty acid and the like as the carrier and serves to suppress cerebral vasospasm, and also suggests that the timing of drug release can be controlled.

In order to effectively prevent or treat certain diseases as described above, including cerebral vasospasm accompanying abnormal contractions of cerebral blood vessels observed after a definite period of time has elapsed after the rupture of a cerebral aneurysm, it is important to release the drug with controlled timing instead of releasing it simply in a steady manner. For example, the above-described cerebral vasospasm comprehends early spasm observed within 24 hours after the rupture of a cerebral aneurysm and delayed spasm observed 4 days to 2 weeks after that, and the latter is considered to be of particular interest from a clinical point of view.

Under these circumstances, it would be meaningful to provide a pharmaceutical preparation in which the timing of drug release can be controlled as described in Japanese Patent Application No. 50953/'94, i.e., a major portion of the drug can be concentratively released after the lapse of a predetermined period of time (which preparation will be referred to herein as a "delayed drug-releasing type" pharmaceutical preparation).

Although delayed drug-releasing type pharmaceutical preparations have already been provided as described above, it is still desired to provide a further improved pharmaceutical preparation or drug delivery system having such a mode of drug release. Accordingly, an object of the present invention is to provide a drug delivery system of the delayed releasing type which can release the drug concentratively after the lapse of a predetermined period of time, instead of releasing it steadily.

SUMMARY OF THE INVENTION

The present inventors have carried on investigations on the development of a drug delivery system of the delayed releasing type by using, as the drug-carrying matrix, an α-hydroxycarboxylic acid polymer which has a good affinity for living bodies and produces little side effect. As a result, it has unexpectedly been found that, although such a polymer itself shows a parabolic degradation pattern in vivo, microspheres prepared by the so-called submerged drying W/O/W process involving the formation of a W/O emulsion by the emulsification of an oil phase containing a specific biodegradable α-hydroxycarboxylic acid polymer and an aqueous phase containing a drug exhibit the above-described delayed drug-releasing behavior.

Thus, as a means for solving the above-described problem, the present invention provides delayed drug-releasing microspheres prepared by a process comprising (A) the step of emulsifying an aqueous solution containing a drug and a water-immiscible solution containing a biodegradable α-hydroxycarboxylic acid polymer to form a W/O emulsion, and (B) the step of emulsifying the emulsion resulting from step (A) in an aqueous solution to form a W/O/W emulsion.

In one preferred embodiment, the present invention provides such microspheres adapted to cerebral implantation and, in particular, such microspheres adapted to cerebral implantation for the purpose of suppressing cerebral vasospasm.

Moreover, the present invention also provides a method for the prophylaxis or treatment of cerebral vasospasm by administering the above-described microspheres to a patient subject to the disease and, in particular, by implanting the above-described microspheres in the brain of the patient.

In a further embodiment, the present invention also provides the use of the above-described microspheres for the making of a pharmaceutical preparation useful in the suppression of cerebral vasospasm.

The microspheres of the present invention have a unique effect in that, even if the α-hydroxycarboxylic acid polymer itself shows a parabolic degradation pattern in the living body, they begin to release a required amount of the drug after the lapse of a predetermined period of time, without entailing a premature burst of the drug.

BRIEF DESCRIPTION OF THE DRAWINGS

FIGS. 1A, 1B and 1C are includes electron micrographs of microspheres in accordance with the present invention, showing the particle structures of several fractions having different particle diameters;

DETAILED DESCRIPTION OF THE INVENTION

Figure 2:
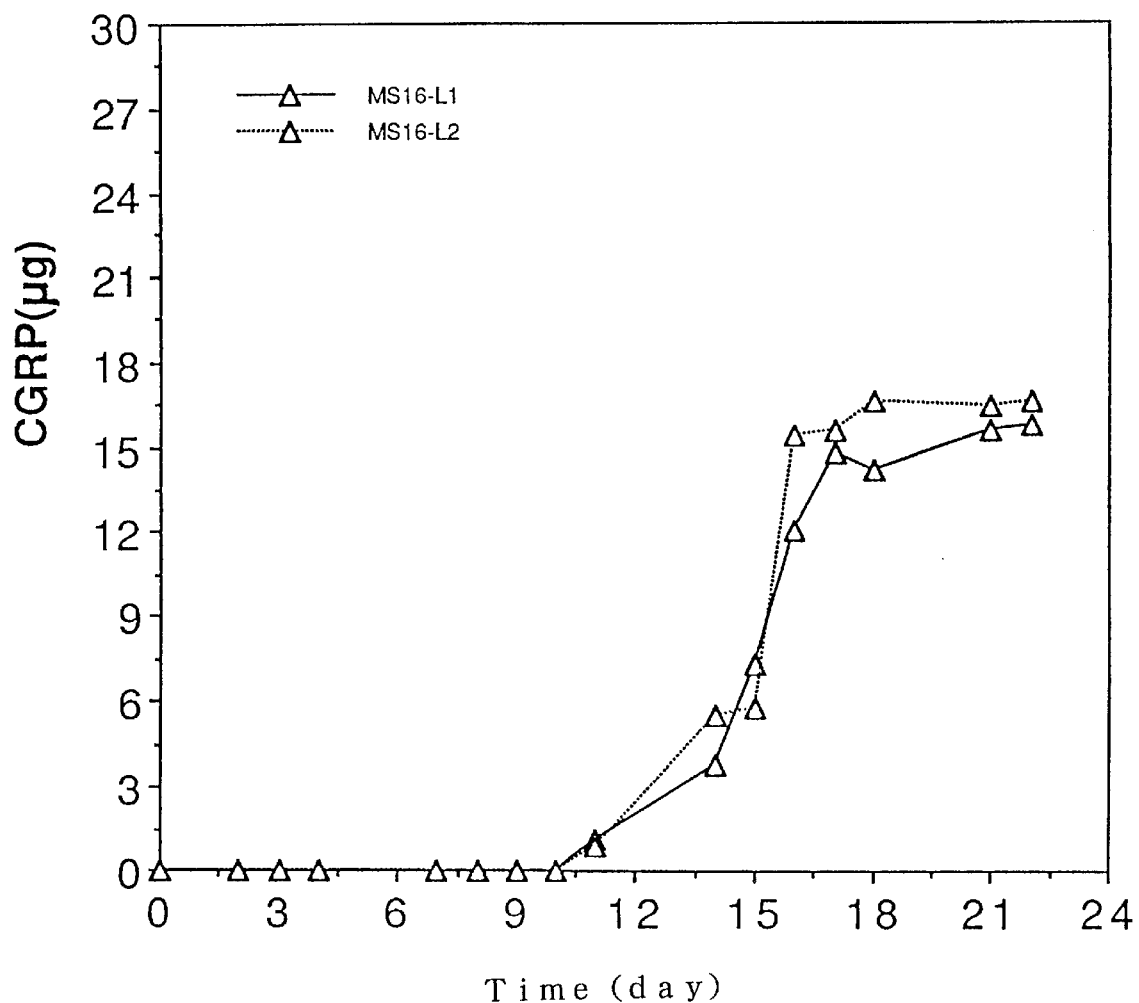
FIG. 2 is a graph showing the in vitro drug-releasing behavior of microspheres in accordance with the present invention (particle diameter: greater than 150 μm)

The aqueous solution containing a drug, which is used to prepare microspheres in accordance with the present invention, can be prepared simply by dissolving the drug in sterilized purified water. In order to improve the solution stability of the drug, this aqueous solution may further contain a buffer agent (e.g., a phosphate buffer or a citrate buffer), osmo regulators (e.g., saccharides such as glucose, lactose, mannitol and sorbitol, and inorganic salts such as sodium chloride), and water-soluble polymers such as gelatin, alginine and gum arabic.

The drug contained in the aqueous solution can be any of various physiologically active substances, provided that they are suited to the objects of the present invention. Specific examples of the drugs intended for use in the present invention include adrenaline, abscisic acid, arginine vasotocin, angiotensinogen, angiotensin, angiotensin I converting enzyme, succus gastricus-inhibiting polypeptides, insulin, insulin-like growth factors, S-factor, erythropoietin, luteinizing hormone, luteinizing hormone-releasing hormone, progestogens, oxytocin, 2-octyl-γ-bromoacetoacetate, autacoids, gastrin, gastrin secretion-accelerating peptide, gastron, activated vitamin $D_3$, kallidin, calcitonin, calcitonin gene-related peptide (CGRP), maxadilans, kininogen, thymus hormone, glucagon, glucocorticoids, vasoactive intestinal peptide, plasma kallikrein, serum factor, blood glucose-elevating hormone, thyroid-stimulating hormone, thyrotropin-releasing hormone, thyroid hormone, melanophore-stimulating hormone, melanophore-stimulating hormone-releasing hormone, melanophore-stimulating hormone release-inhibiting hormone, corticotropin-like middle lobe peptide, urokinase, cholecystokinin octapeptide, cholecystokinin tetrapeptide, cholecystokinin variant, cholecystokinin-12, cholecystokinin pancreothymine, cholecystokinin, growth factor, substance P, female sex hormones, adipokinin, chorionic gonadotropin, nerve growth factor, pancreatic polypeptides, gonad-stimulating substance, gonadotropic hormones, growth hormone, growth hormone-releasing factor, secretin, caerulein, serotonin, fibroblast growth factor, kallikrein glandularis, somatostatin, somatomedins A and B, placental lactogen, thymosin, thymopoietin, thyroglobulin, traumatic acid, endothelial cell growth factor, mollusc heart stimulant neuropeptide, neurotensin, equine serum gonadotropic hormone, brain hormones, noradrenaline, vasopressin, estrogenic hormone, histamine, epidermic cell growth factor, parathyroid hormone, parathyroid-stimulating hormone, corticotropin-releasing factor, adrenocortical hormones, PACAP, bradykinin, bradykinin-like peptide, proinsulin, proopiomelanocortin, prostaglandins, pro PTH, prolactin, prolactin-releasing hormone, prolactin release-inhibiting hormone, florigene, human menopausal gonadotropin, bombesine, mineral corticoid, light adaptation hormone, methionyllysylbradykinin, 1-methyladrenaline, melatonin, motilin, androgen, diuretic hormone, lipotropin, renin, relaxin and follicle maturation hormone.

The drugs having the effect of suppressing cerebral vasospasm, which are particularly intended for use in the present invention, include CGRP, maxadilans, deferoxamine, methylprednisolone, nicorandil, nicaraben, magnesium sulfate, actinomycin D, 21-aminosteroid, isoproterenol, tPA, urokinase, nimodipine, hydrocortisone, nicardipine, nifedipine, diltiazem, dilazep, teprothid, AA 861, papaverine, OKY 1581, amyl nitrite, erythrityl tetranitrate, isosorbide dinitrate, nitroglycerin, pentaerythritol tetronitrate, VIP, vasopressin, bradykinin, PACAP, SOD, catalase, bepridil, nadololol, felodipine, isradipine, verapamil, atenolol, metoprolol and propranolol.

Among these drugs, CGRP and maxadilans are deeply intended for use in the present invention. When these peptides (or proteins) are formed into microspheres in accordance with the present invention, they can be effectively used because, in cooperation with the biodegradability of the α-hydroxycarboxylic acid polymer used and the solubility of the drugs themselves in body fluids, they exhibit unique drug-releasing behavior desired in the present invention. In this connection, the maxadilans which can be used in the present invention include proteins found in the salivary gland of the sand fly (*Lutzomyia longipalpis*) as described, for example, in E. A. Lerner, J. Biol. Chem., 267, 1062–1066 (1992), and analogous proteins as described in International Publication No. WO 95/04829.

The concentration of the drug in the aqueous solution cannot be clearly defined because it depends on the type of the drug used, and the type and severity of the disease to be treated. However, the drug should preferably be used at such a concentration as not to cause an excessive premature release (or burst) from the microspheres during treatment. By way of example, CGRP is usually used at a concentration of $1 \times 10^{-8}$ to 100 mg/l and preferably $1 \times 10^{-5}$ to 1 mg/l, though the present invention is not limited thereto.

The biodegradable α-hydroxycarboxylic acid polymers which can be used to form the polymeric matrix of microspheres in accordance with the present invention include, for example, homopolymers derived from one of glycolic acid, lactic acid, 2-hydroxybutyric acid, 2-hydroxyvaleric acid and 2-hydroxy-3-methylbutyric acid, as well as copolymers derived from two or more of the foregoing compounds. Among these polymers, homopolymers of lactic acid and copolymers of lactic acid and glycolic acid can conveniently be used because their characteristics as polymeric matrices for carrying drugs have been studied well and commercial products having various degrees of polymerization are available. The lactic acid used as a monomer may be its D- or L-isomer or a mixture containing its D- and L-isomers in any desired proportion, and polymers so prepared are commercially available.

In view of the objects of the present invention, when CGRP is chosen as the drug, it is especially preferable to use a copolymer prepared from a monomer mixture composed of L-lactic acid and glycolic acid in a molar ratio of 7:3 to 3:7 and having a molecular weight of about 4,000 to 11,000 as measured by gel permeation chromatography (GPC).

The water-immiscible solution containing a polymer as described above is usually prepared by dissolving the polymer in a halogenated hydrocarbon such as methylene chloride, chloroform or dichloroethane. However, methylene chloride is preferably used because it can be easily evaporated. The concentration of the polymer in this solution may generally be in the range of 10 to 100% by weight and preferably 50 to 80% by weight.

According to the present invention, the aqueous solution containing the above-described drug and the water-immiscible polymer solution are subjected to an emulsification treatment. This treatment is preferably carried out under such conditions as to produce a W/O emulsion in which most of the oil droplets contained therein have an average diameter of about 0.5 to 5 μm. The reason for this is that excessively small oil droplets may not exhibit the desired delayed drug-releasing behavior, and excessively large oil droplets may have low stability.

When the emulsification treatment is carried out, for example, by the application of ultrasonic waves, the mixed system may be ultrasonicated under ice cooling for one to several minutes by means of a commercially available ultrasonic homogenizer [e.g., Sonifier-250 (manufactured by BRANSON)]. Mechanical stirring may be used in combination with the ultrasonication. In such a case, good results will be produced by performing the mechanical stirring at a speed of about 10,000 rpm or greater.

In this emulsification treatment, one or more additives selected from surfactants and water-soluble polymers which contribute to the stabilization of the W/O emulsion may be added to the mixed system. Usable surfactants include anionic surfactants such as sodium oleate, sodium stearate and sodium lauryl sulfate, and nonionic surfactants such as polyoxyethylene sorbitan fatty acid esters, and usable water-soluble polymers include polyvinyl alcohol, polyvinyl pyrrolidone, carboxymethylcellulose, hydroxypropylcellulose, gelatin and the like. These additives may be used at such a concentration as to give a 0.01 to 10%(w/w) aqueous solution.

Subsequently, the W/O emulsion prepared in the above-described manner is emulsified with an aqueous solution constituting an outer aqueous phase to form a W/O/W emulsion. It is especially preferable to add the above-described emulsion stabilizer to this outer aqueous phase at the above-defined concentration. When methylene chloride is used as the solvent for the polymer, the solvent can be evaporated under submerged conditions by carrying out the emulsification treatment at room temperature by vigorous stirring (e.g., at a speed of about 10,000 rpm or greater). Consequently, microspheres containing the drug in the polymer matrix are formed in the water. In order to promote the evaporation of the solvent, the above-described treatment may be carried out under reduced pressure.

If necessary, the microspheres may be stabilized by stirring the emulsion under milder conditions (e.g., at about 500 rpm) for several hours. Thereafter, the microspheres are separated by precipitation (or centrifugation) or filtration, washed, and then vacuum-dried or freeze-dried. Thus, there can be obtained microspheres in accordance with the present invention. In certain cases, these microspheres may be classified by sieving.

The microspheres thus obtained exhibit delayed drug-releasing behavior in body fluids or simulated body fluids [e.g., Hartmann's fluid (manufactured by Green Cross Corporation)], without entailing a premature burst of the drug. By way of example, mention is made of microspheres prepared in accordance with the present invention by using CGRP as the drug and a lactic acid-glycolic acid copolymer (composed of lactic acid and glycolic acid in a molar ratio of 7:3 to 3:7 and having a molecular weight of about 4,000 to 11,000 as measured by GPC) as the polymer. When they are suspended in a simulated body fluid and maintained at 37° C., they exhibit a bulk release of the drug after several days to ten-odd days, and when they are implanted in the brain of an experimental animal, they exhibit a bulk release of the drug after 2 to 8 days. In order to achieve the above-described drug-releasing behavior, microspheres having diameters of about 30 to 300 μm are preferred.

Generally, this timing of drug release can be retarded by increasing the proportion of lactic acid used to prepare the polymer. Those skilled in the art will be able to prepare microspheres having a desired timing of drug release by repeating trial runs according to the type of the drug used.

Microspheres in accordance with the present invention can be directly used for intracerebral implantation or oral administration, or can be used in the form of an injectable suspension. They can also be used in other dosage forms according to the route of administration. For example, as a pharmaceutical preparation for use in intracerebral implantation, they may be formed into tablets having a size which does not interfere with intracerebral implantation (e.g., having a thickness of 5 mm or less and, in the case of cylindrical tablets, a diameter of 8 mm or less). Such tablets can be formed according to any technique known per se, using excipients such as lactose, crystalline cellulose and starch (e.g., corn starch), and other commonly used additives such as disintegrators (e.g., carboxymethylstarch sodium and carboxymethylcellulose calcium), binders (e.g., hydroxypropylcellulose, gum arabic, dextrin, carboxymethylcellulose, methylcellulose and polyvinyl pyrrolidone) and lubricants (e.g., talc, magnesium stearate and polyethylene glycol 6000).

According to the present invention, there are provided microspheres which can release a major portion of the drug after a predetermined period of time has elapsed after administration of the pharmaceutical preparation, without entailing a premature burst of the drug. Consequently, when microspheres in accordance with the present invention are prepared by using, for example, a drug having the effect of suppressing cerebral vasospasm, they can treat that disease conveniently. Moreover, there is also provided a pharmaceutical preparation which is adapted to intracerebral implantation and hence more effective in such treatment.

The present invention will be more clearly understood with reference to the following examples using CGRP as a drug. However, these examples are not to be construed to limit the scope of the invention.

EXAMPLE 1

Preparation of Microspheres 6 mg of CGRP was dissolved in 0.5 ml of distilled water for injection use. On the other hand, 10 g of a copolymer derived from L-lactic acid and glycolic acid (in a molar ratio of 1:1) [having a molecular weight of about 4,500 as measured by GPC and corresponding to PLG 1600ML commercially available from Kokusan Chemical Co., Ltd.] was dissolved in 10 g of methylene chloride. After the solutions so prepared were mixed, the resulting mixture was agitated by means of an ultrasonic homogenizer [Sonifier-250 (manufactured by BRANSON)] for one minute under ice cooling to form a W/O emulsion.

This emulsion was added to 2,500 ml of a separately prepared 0.1%(w/w) aqueous solution of polyvinyl alcohol, and the resulting mixture was stirred at about 10,000 rpm [by means of a D-7801 homogenizer (manufactured by Ystral GmbH)] for 5 minutes under ice cooling (at about 15° C.) to form a W/O/W emulsion. This emulsion was further stirred at about 500 rpm [by means of a Three-One Motor (manufactured by Shinto Scientific Co., Ltd.)] at room temperature (about 25° C.) for 3 hours. After the resulting emulsion was centrifuged and the supernatant was discarded, the separated microspheres were washed with distilled water on a membrane filter (manufactured by Millipore Ltd.) having a pore diameter of 0.4 μm. The washed microspheres were placed in a vacuum dryer (at room temperature) and dried under reduced pressure for 48 hours. Thus, microspheres predominantly having diameters in the range of about 40 to 100 μm were obtained in a total amount of 5 g.

These microspheres (hereinafter referred to as "MS-16") contained 36 μg of CGRP per 60 mg of microspheres.

When these microspheres were classified by means of standard sieves made of stainless steel, a fraction having an average particle diameter of greater than 150 μm [hereinafter referred to as MS-16(L)], a fraction having an average particle diameter of 150 to 32 μm [hereinafter referred to as MS-16(M)], and a fraction having an average particle diameter of less than 32 μm [hereinafter referred to as MS-16(S)] comprised 15%, 53% and 32%, respectively. Electron micrographs of these fractions are shown together in FIGS. 1A, 1B and 1C.

EXAMPLE 2

Formation of a Tablet from Microspheres 60 mg of MS-16 obtained in Example 1 was intimately blended with 1.8 mg of hydroxypropylcellulose and 0.6 mg of magnesium stearate. Using a Correct N-30E single-shot tableting machine (manufactured by Okada Seiko Co., Ltd.), the resulting blend was pressed into a tablet (6 mmφ×2 mm).

Drug release tests (1) In vitro test

Figure 3:
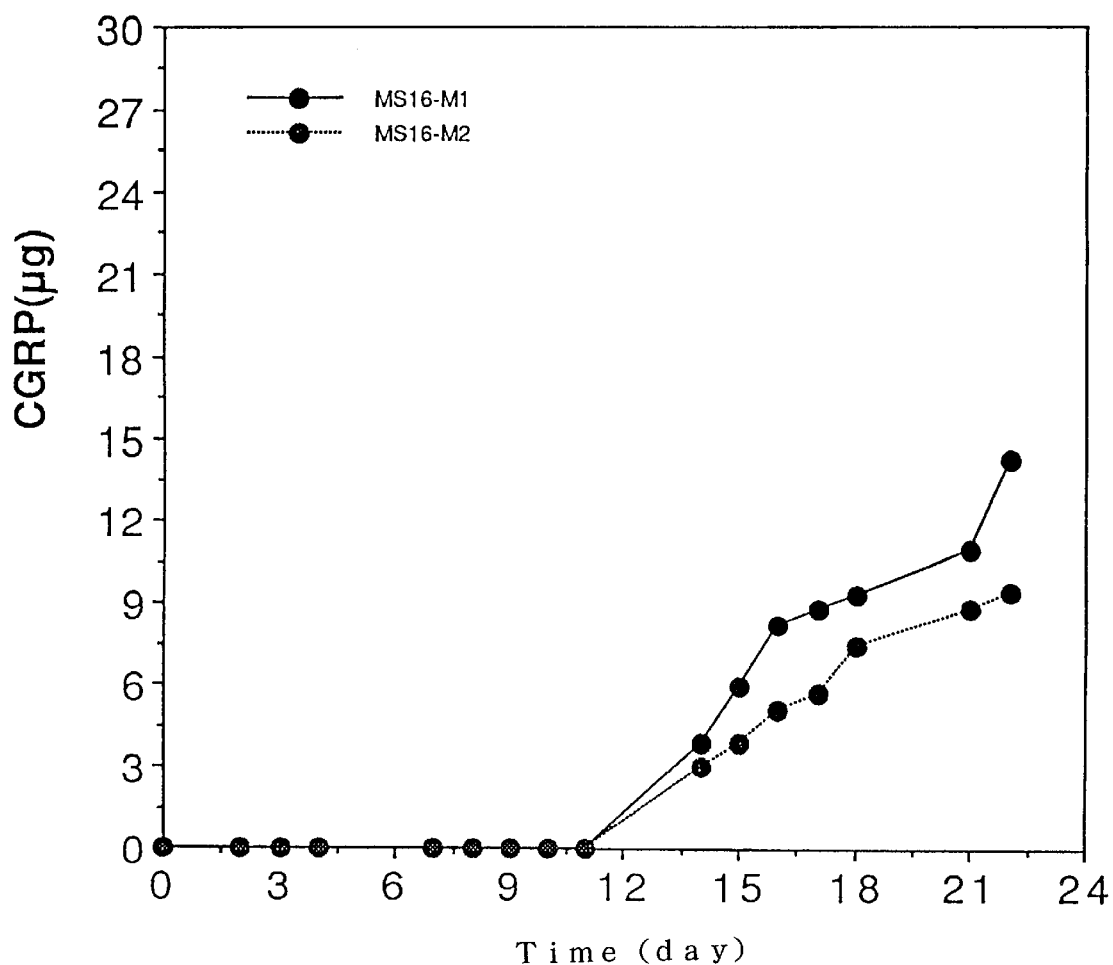
FIG. 3 is a graph showing the in vitro drug-releasing behavior (in two runs) of microspheres in accordance with the present invention (particle diameter: 32 to 150 μm)
Figure 4:
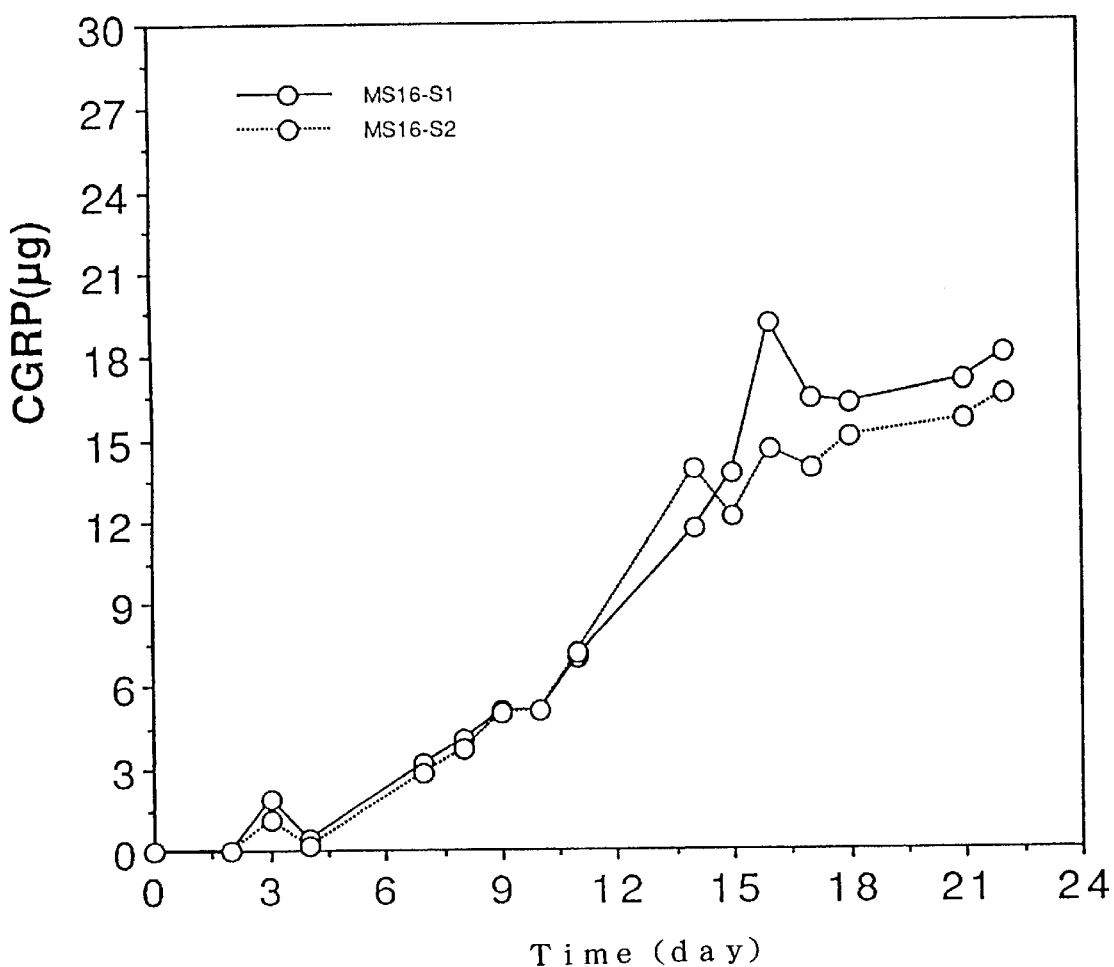
FIG. 4 is a graph showing the in vitro drug-releasing behavior (in two runs) of microspheres in accordance with the present invention (average particle diameter: less than 32 μm)

Tubes having a capacity of 15 ml were sterilely charged with 5 ml of Hartmann's solution (manufactured by Green Cross Corporation). Then, 60 mg each of MS-16(L), MS-16(M) and MS-16(S) obtained in Example 1 were separately added to the tubes under sterile conditions. While these tubes were allowed to stand at 37° C., the solution was sampled from each tube at time 0 and appropriate times between the 1st and 14th days, and analyzed by high-performance liquid chromatography (HPLC) to determine the amount of CGRP released into Hartmann's solution. The amount of CGRP released was plotted as a function of time to obtain graphs showing the respective drug-releasing patterns. These graphs are given in FIGS. 2, 3 and 4.

The conditions employed for HPLC were as follows:

Mobile phase:
  Liquid A: A 0.1% aqueous solution of trifluoroacetic acid (TFA).
  Liquid B: A 0.085% solution of TFA in $CH_3$ CN. (A concentration gradient was created in such a way that the proportion of liquid B increased from 20% to 60% over a period of 20 minutes.)
  Column: Capsule Pack $C_8$ SG300 (manufactured by Shiseido Co., Ltd.; 6 mmφ×35 mm).
  Flow rate: 1.5 l/min.
  Detection: 214 nm.

It can been from the respective figures that, in particular, the microspheres having diameters of 32 μm or greater released CGRP from 10 or 11 days after the start of the test, without entailing a premature burst of the drug.

(2) In vivo test (Implantation of a pharmaceutical preparation in the brain)

Five rabbits (weighing 2.5 to 3.0 kg) were anesthetized with pentobarbital (50 mg/kg for each animal) and fixed in a prostrate position. An incision was made in the head to expose the occipital periosteum (or dura mater), and the occipital bone was drilled to expose more of the dura mater. Thereafter, an about 8 mm incision was made in the dura mater and the arachnoidea, and a pharmaceutical preparation was implanted therethrough. For this purpose, 60 mg of MS-16 obtained in Example 1 was used in two of the five animals, one tablet obtained in Example 2 in other two animals, and one placebo tablet (not containing CGRP) in the remaining one animal. After the dura mater, muscles and skin were sutured, an appropriate dose of an antibiotic was administered to the site of incision.

Cerebrospinal fluid was collected daily from the aforesaid rabbits according to the following collection method, and the CGRP concentration (in nM) in the cerebrospinal fluid was measured according the following measuring method.

(Method for the collection of cerebrospinal fluid)

The above rabbits were anesthetized with pentobarbital and fixed in a prostrate position. An incision was made in the head to expose the occipital periosteum (or dura mater). Then, an incision was made in the occipital periosteum and cerebrospinal fluid (CSF) was collected through this incision.

(Method for the measurement of the CGRP concentration in cerebrospinal fluid)

This method comprises a radioimmunoassay procedure as described below.

Figure 5:
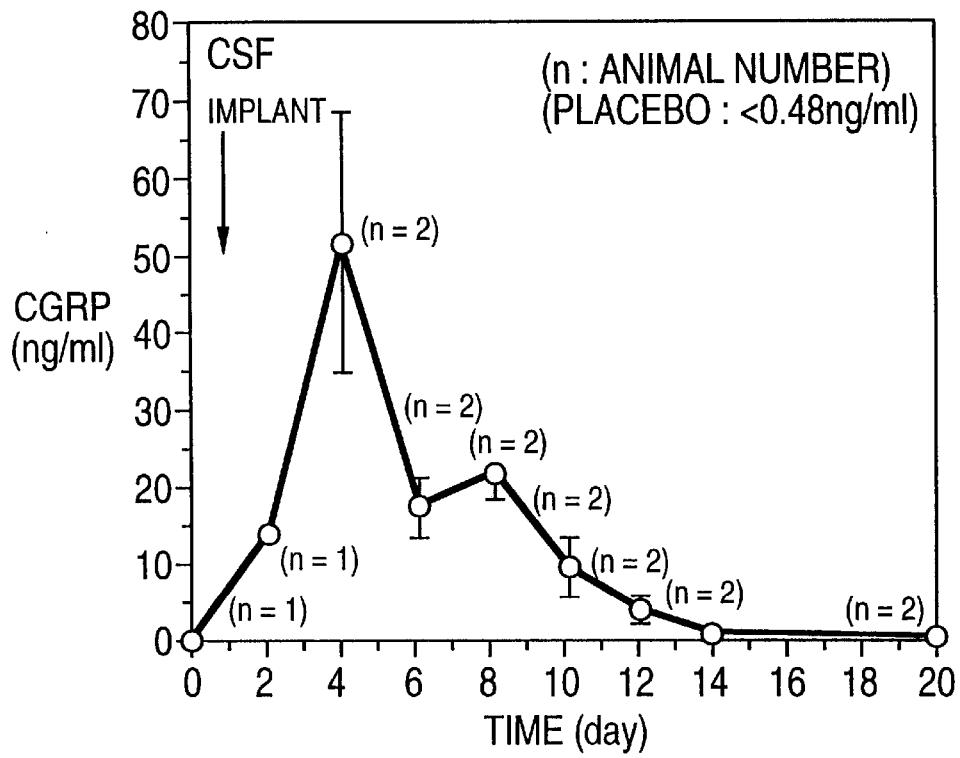
FIG. 5 is a graph showing the in vivo drug-releasing behavior of microspheres in accordance with the present invention.
Figure 6:
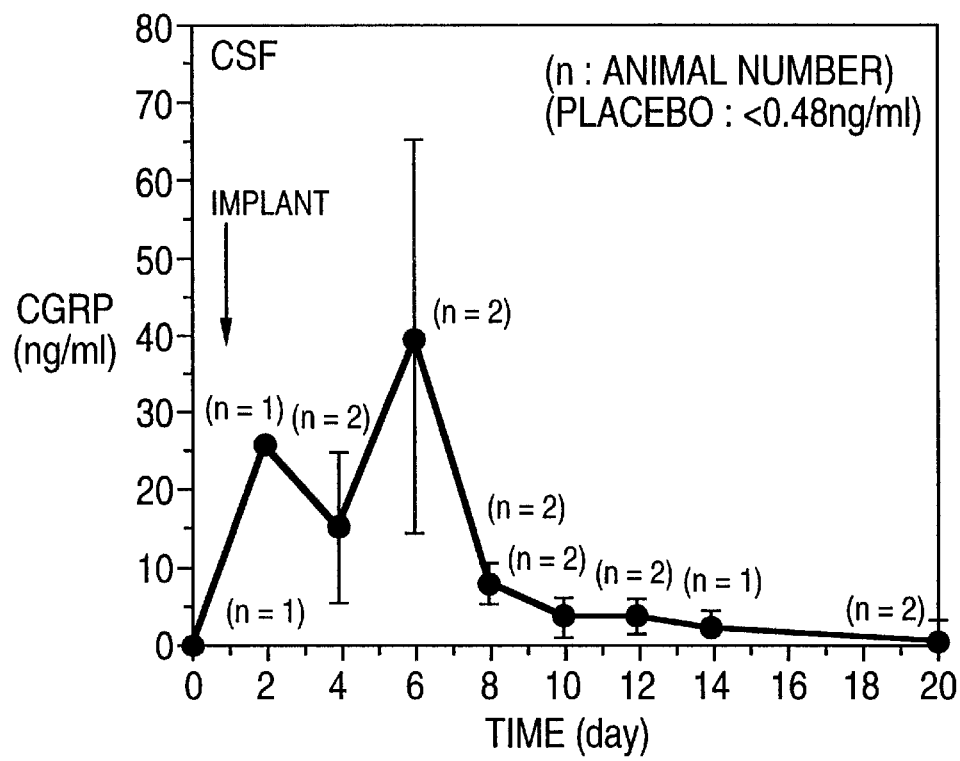
FIG. 6 is a graph showing the in vivo drug-releasing behavior of a tablet formed from microspheres in accordance with the present invention.

Measuring tubes were charged with 4000 cpm of a labeled compound [2-($^{125}$I-iodohistidy$^{10}$) CGRP]. Separately, 100 μl each of 1, 2, 5, 10, 50, 100, 500 and 1000 fmol standard solutions were prepared by using synthetic CGRP (manufactured by Bachem) as a standard substance. To the tubes containing 100 μl of a test sample, a standard solution or water were added 100 μl of an antibody solution [prepared by dissolving RPN 1841 (manufactured by Amersham) in 2 ml and diluting the solution to 12.5 ml] and 600 μl of an analytical buffer solution [50 mM sodium phosphate (pH 7.4), 0.3% bovine serum albumin, 10 mM EDTA]. These tubes were covered and allowed to stand at 4° C. for 5 days. Then, 250 μl of a dextran/charcoal solution [50 mM sodium phosphate (pH 7.4), 0.25% gelatin, 10 mM EDTA] was added to the tubes, which were immediately centrifuged at 2000×g for 20 minutes. Using a gamma counter, both the precipitate and the supernatant were counted for 200 seconds. Then, the concentration of the physiologically active substance (CGRP) in CSF was determined by reference to a standard curve constructed with the solutions of the standard substance. The results obtained with MS-16 and tablets are shown in FIGS. 5 and 6, respectively.

It can be seen from these figures that, when MS-16 or a tablet formed therefrom is implanted in the brain of animals, it releases a major portion of CGRP concentratively after a predetermined period of time has elapsed after its implantation.

What is claimed is:

1. Delayed drug-releasing microspheres derived from a W/O/W emulsion which can be prepared by a process comprising
  (A) the step of emulsifying an aqueous solution containing a drug and a water-immiscible solution containing a biodegradable α-hydroxycarboxylic acid polymer to form a W/O emulsion, and
  (B) the step of emulsifying the emulsion resulting from step (A) in an aqueous solution to form a W/O/W emulsion,
  wherein said drug is a peptide having the effect of suppressing cerebral vasospasm, and wherein
  (i) in an in vivo drug-releasing test, said microspheres release more than 75% of the drug into body fluids when from 2 to 10 days have passed after the microspheres make contact with the fluids, and (ii) in an in vitro drug-releasing test, said microspheres release less than 10% of the drug into simulated body fluids when 5 days have passed after the microspheres make contact with the fluids.

2. Microspheres as claimed in claim 1 wherein the drug is selected from the group consisting of calcitonin gene-related peptide and maxadilans.

3. Microspheres as claimed in claim 1 wherein the biodegradable α-hydroxycarboxylic acid polymer is a polymer of lactic acid or a copolymer of lactic acid and glycolic acid.

4. Microspheres as claimed in claim 1 wherein the formation of an emulsion in step (A) is carried out by ultrasonication.

5. A method for the prophylaxis or treatment of human cerebral vasospasm by administering a pharmaceutical preparation to a patient whose cerebral aneurysm is expected to rupture or has ruptured, wherein the pharmaceutical preparation comprises delayed drug-releasing microspheres prepared by a process comprising (A) the step of emulsifying an aqueous solution containing a drug and a water-immiscible solution containing a biodegradable α-hydroxycarboxylic acid polymer to form a W/O emulsion, and (B) the step of emulsifying the emulsion resulting from step (A) in an aqueous solution to form a W/O/W emulsion, wherein said drug is a peptide having the effect of suppressing cerebral vasospasm, and wherein (i) in an in vivo drug-releasing test, said microspheres release more than 75% of the drug into body fluids when from 2 to 10 days have passed after the microspheres make contact with the fluids, and (ii) in an in vitro drug-releasing test, said microspheres release less than 10% of the drug into simulated body fluids when 5 days have passed after the microspheres make contact with the fluids and wherein said administering is conducted by the implantation of the pharmaceutical preparation in the brain.

6. The method as claimed in claim 5 wherein the drug is selected from the group consisting of calcitonin gene-related peptide and maxadilans.

7. The method as claimed in claim 5 wherein the biodegradable α-hydroxycarboxylic acid polymer is a polymer of lactic acid or a copolymer of lactic acid and glycolic acid.

8. The method as claimed in claim 5 wherein the formation of an emulsion in step (A) is carried out by ultrasonication.

9. Microspheres as claimed in claim 1 which have a mean diameter of about 30 to 300 μm.

10. The method as claimed in claim 5 wherein the microspheres have a mean diameter of about 30 to 300 μm.

11. The method as claimed in claim 5, wherein the administering is conducted by the intracerebral implantation of the pharmaceutical preparation.

* * * * *